US006821262B1

(12) United States Patent
Muse et al.

(10) Patent No.: US 6,821,262 B1
(45) Date of Patent: Nov. 23, 2004

(54) SELF OPERABLE KNEE EXTENSION THERAPY DEVICE

(76) Inventors: Richard R. Muse, 1158 Crumbaugh Pike, Georgetown, KY (US) 40324; James M. Hartford, 2148 Ami La., Lexington, KY (US) 40516

( * ) Notice: Subject to any disclaimer, the term of this patent is extended or adjusted under 35 U.S.C. 154(b) by 126 days.

(21) Appl. No.: 09/944,321

(22) Filed: Aug. 31, 2001

(51) Int. Cl.[7] .................................................. A61F 5/00

(52) U.S. Cl. ............................ 602/26; 128/882; 602/35

(58) Field of Search ................................ 602/5, 23, 26, 602/27, 35; 128/846, 882; 482/91, 907; 601/33, 34

(56) References Cited

U.S. PATENT DOCUMENTS

| | | | |
|---|---|---|---|
| 4,542,900 | A | 9/1985 | Ray |
| 4,844,454 | A | 7/1989 | Rogers |
| 5,013,037 | A | 5/1991 | Stermer |
| 5,088,731 | A | 2/1992 | Carpenter |
| 5,167,612 | A | 12/1992 | Bonutti |
| 5,213,094 | A | 5/1993 | Bonutti |
| 5,236,333 | A | 8/1993 | Barba, Jr. |
| 5,254,060 | A | 10/1993 | Bohanan |
| 5,254,067 | A | 10/1993 | Habing et al. |
| 5,285,773 | A | 2/1994 | Bonutti et al. |
| 5,338,274 | A | 8/1994 | Jones |
| 5,395,303 | A | 3/1995 | Bonutti et al. |
| 5,456,268 | A | 10/1995 | Bonutti |
| 5,509,894 | A | 4/1996 | Mason et al. |
| 5,611,770 | A | 3/1997 | Tesch |
| 5,662,562 | A | 9/1997 | Wohlenberg |
| 5,685,830 | A | 11/1997 | Bonutti |
| 5,803,883 | A | 9/1998 | Patrylak et al. |
| 5,855,538 | A | 1/1999 | Argabright |
| 5,897,459 | A | 4/1999 | Habing et al. |

*Primary Examiner*—Michael A. Brown
(74) *Attorney, Agent, or Firm*—Kevan Morgan

(57) ABSTRACT

A device for exercising a patient's leg, including rehabilitating a patient's knee joint following knee surgery is disclosed. The device comprises an elongated member with a handle at one end, a harness for holding the patient's foot attached to the other end, and an adjustable slider assembly that can be positioned at a variety of locations along the elongated member. A fulcrum, which is attached to the slider assembly rests on the top of the patient's leg, either above or below the knee, while the harness holds the patient's foot. The device is operated by the patient pulling on the handle, thereby straightening the leg, which increases the range of motion of the knee joint following knee surgery. The device is adjustable to accommodate patients of varying heights and leg lengths and also to provide greater leverage in operating the device.

7 Claims, 3 Drawing Sheets

Fig. 3
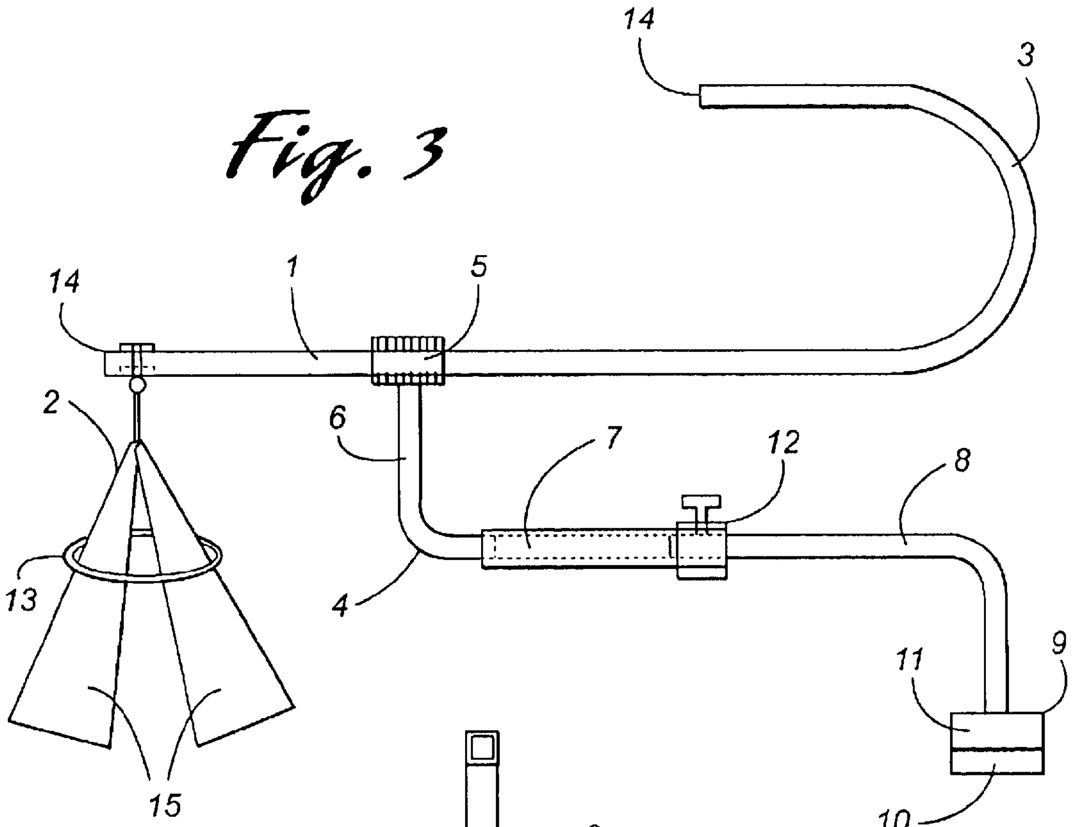
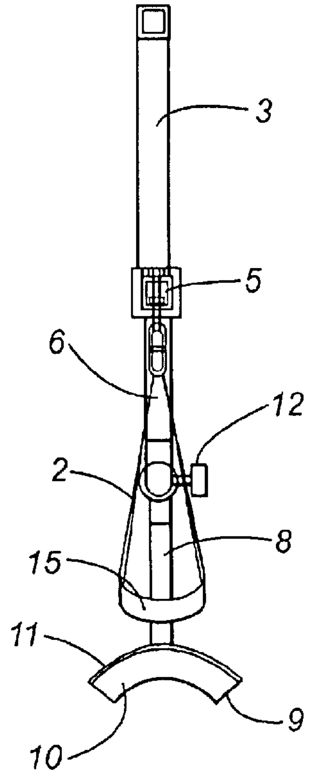
Fig. 4

SELF OPERABLE KNEE EXTENSION THERAPY DEVICE

BACKGROUND OF THE INVENTION

This invention relates generally to a device: for exercising the leg and/or providing rehabilitative therapy of a patient's leg and knee joint. In many situations, it is desirable for a patient to manually exercise the knee joint. Two such situations are anterior crucial ligament (ACL) knee surgery and knee replacement surgery, where the range of motion of the knee joint must be increased following the surgery to allow the patient to perform normal activities. The process of regaining the full range of motion of the knee joint is slow and a device such as the present invention speeds that process by allowing the patient to manually extend the leg through the full range: of motion. This therapy normally comes with some discomfort, so a manual device is preferable to an automatic exerciser, so that the patient may control the amount of pressure applied to exercise the knee joint or straighten the leg.

In the United States, there are over one million ACL and knee replacement surgeries each year. Outside of the U.S., however, there are over ten million ACL and knee replacement surgeries each year. The present invention provides a much needed, simple, and relatively inexpensive device for not only rehabilitative therapy following ACL or knee replacement surgery, but also for exercising a patient's leg generally.

DESCRIPTION OF THE PRIOR ART

The prior art contains numerous devices for exercising the leg and/or rehabilitating the knee joint of a patient. However, none of the prior art combines the simplicity, high degree of adjustability, effectiveness, and low cost of the claimed invention.

U.S. Pat. No. 5,662,562 to Wohlenberg teaches a leg exercise device that can be placed above or below the knee.

U.S. Pat. No. 5,236,333 to Barba, Jr. teaches a leg exerciser that is placed directly on the knee joint and operated by the user.

U.S. Pat. No. 4,844,454 to Rogers teaches a knee therapy device using two platforms that secure the upper and lower portions of the leg.

U.S. Pat. No. 5,254,060 to Bohannon teaches a motorized apparatus to exercise the legs or arms of a patient.

U.S. Pat. Nos. 5,896,459 and 5,254,067 to Habing et al. teach leg exercise devices that use pistons or a flywheel and generator to provide resistance to leg movement.

U.S. Pat. No. 5,803,883 to Patrylak et al., U.S. Pat. No. 5,338,274 to Jones, and U.S. Pat. No. 4,542,900 to Ray teach exercise devices that employ weights, similar to machines found in gymnasiums.

U.S. Pat. No. 5,855,538 to Argabright teaches a device that allows the user to position his feet in members that slide along tracks to extend the legs.

U.S. Pat. Nos. 5,685,830, 5,456,268, 5,395,303, 5,285,773, 5,213,094, and 5,167,612 to Bonutti teach complex mechanical devices utilizing wires, pulleys, and cuffs to exercise or rehabilitate a patient's arm, although '094 discloses application to a knee joint as well.

U.S. Pat. No. 5,088,731 to Carpenter teaches a device for exercising the wrist of a patient.

U.S. Pat. No. 5,611,770 to Tesch teaches a device for exercising the foot or ankle of a patient.

U.S. Pat. No. 5,509,894 to Mason et al. teaches a device that holds the leg in a suspended position and allows the user to pull a handle to straighten the leg, with the only downward force being applied to the leg being that of its own weight.

U.S. Pat. No. 5,013,037 to Stermer teaches a physical therapy device worn by a patient to provide resistance to certain directions of motion.

SUMMARY OF THE INVENTION

While not limited to therapy, this device finds particular application in rehabilitative therapy for patient of knee surgery, as often times the ligaments in the knee joint will heal in a contracted state, and therefore must be stretched in order to regain the full range of motion in the patient's knee joint. Accordingly, It is the object of the present invention to provide a simple, effective, and inexpensive device to exercise the legs and knee joints of persons of varying height, leg length, and upper body strength.

Another object of the present invention is to enable self-directed movement of a leg by a patient that is unable to do so under his own leg muscle control, such as where a person has experienced either temporary or permanent paralysis of the lower body. In such situations, it is desirable to manually exercise the patient's immobile limbs.

The present invention is directed to a lever with a handle on one end with a harness means attached to the other end. A fulcrum is attached to a slider assembly located in the middle portion of the lever. The slider assembly and fulcrum can be adjusted to provided optimum placement of the fulcrum on the patient's leg.

Additionally, the slider assembly and fulcrum can be adjusted to provide the user with greater leverage. While the present invention can be used with the assistance of weights, which would be hung on the handle, it is generally unnecessary to use weights, because of the increased leverage from the present invention. By allowing the user to increase the horizontal distance between the fulcrum and the point where the slider assembly attaches to the lever, thereby increasing the moment arm, the user can effectively increase the leverage of the device by 300–500%. This is particularly useful where the user does not have a great deal of upper body strength or the limb being exercised or straightened requires a higher level of pressure to effectively articulate the limb.

A harness means is located at the end of the lever opposite the handle and is used to hold the foot and ankle in place. The harness means in the preferred embodiment has a means of securing the foot, namely a ring that is used to cinch the two straps, which form the harness. The harness is not only effective to support the foot and ankle, but is also comfortable for the user. The harness allows the users foot to pivot and turn while still providing the support necessary to effectively exercise the leg or knee joint.

A means for fixing the position of the slider assembly and fulcrum relative to the elongated member, such as a handknob or other mechanical means, is also contemplated in the present invention. Other mechanical means could include a rubber grommet affixed to the interior diameter of the slider, which would prevent (except through deliberate positioning by the user) said slider from moving along the elongated member, or holes through said elongated member and a hole in the slider through which a pin could be inserted, thereby fixing their relative positions. The various possible means for fixing the position of the slider relative to the elongated member, although contemplated in the invention, are not shown in the drawings.

BRIEF DESCRIPTION OF THE SEVERAL VIEWS OF THE DRAWING

FIG. 3 is a plan view of the preferred embodiment;

FIG. 4 is a left side view of the preferred embodiment, without the adjusting ring on the harness means (omitted for clarity of the other features)

Referring now to the figures in greater detail, where like reference numbers denote like parts in the various figures.

DETAILED DESCRIPTION OF THE INVENTION

Figure 1:
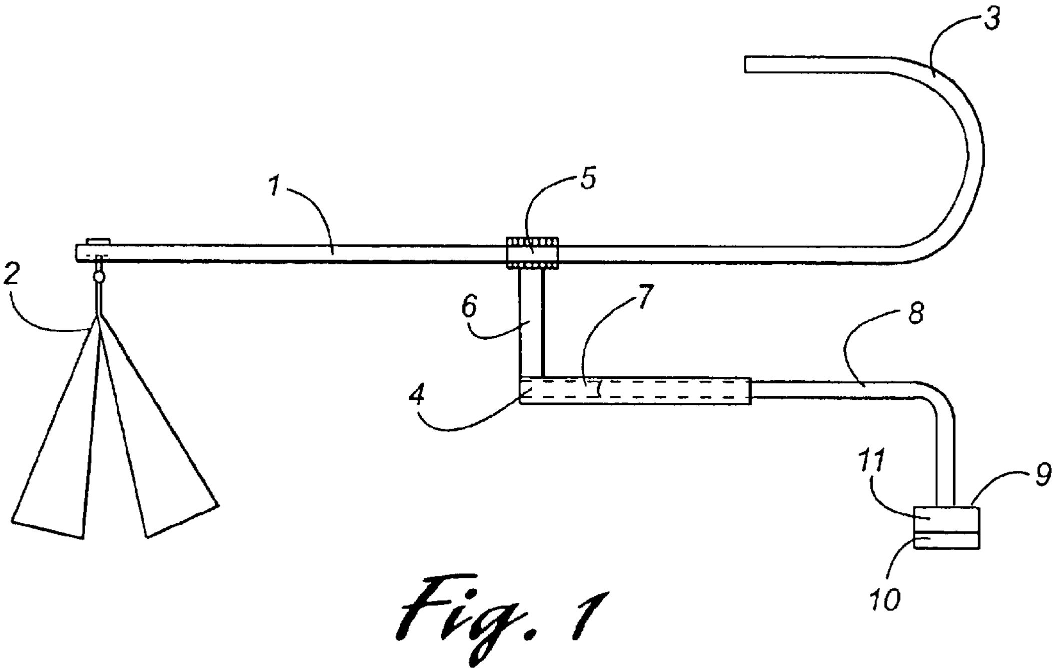
FIG. 1 is a plan view of the invention.
Figure 2:
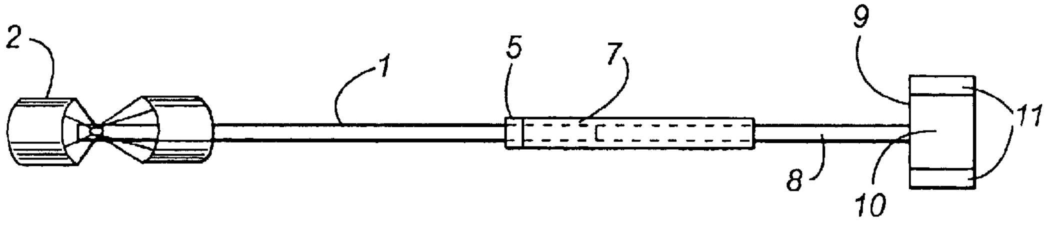
FIG. 2 is a front view of the invention.
Figure 5:
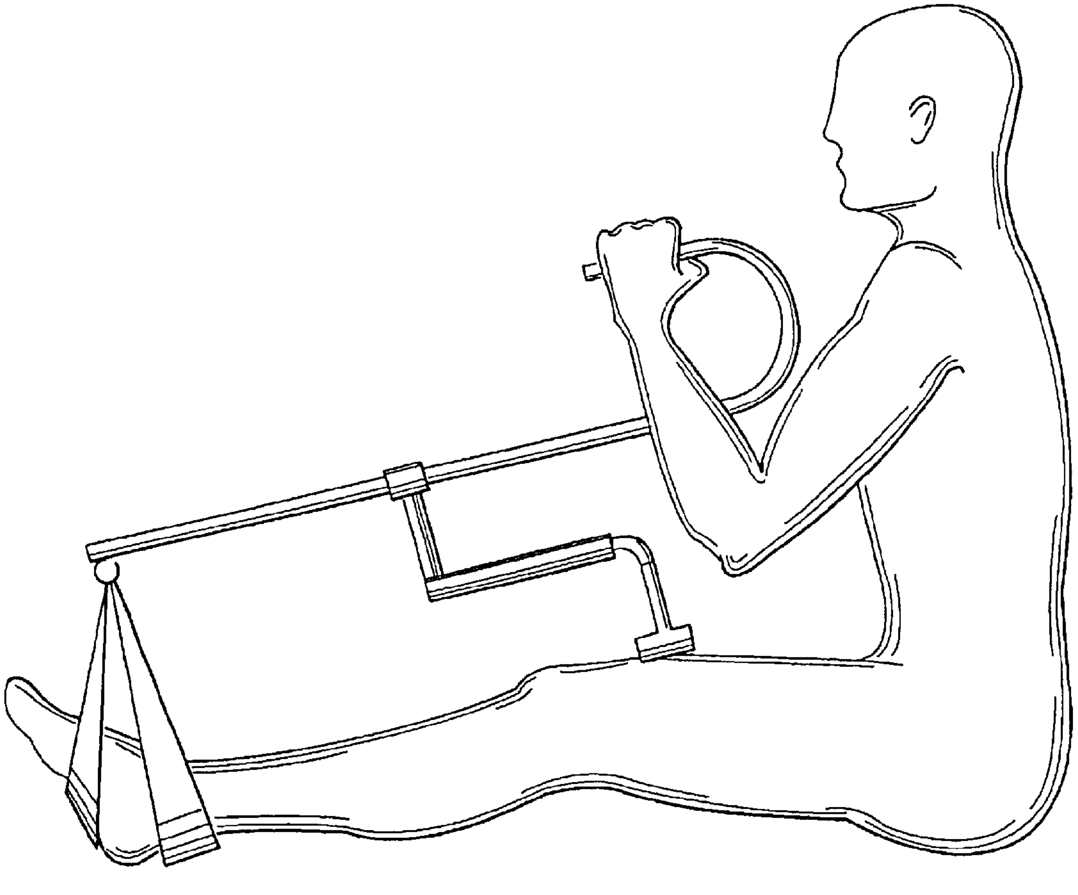
FIG. 5 shows the present invention in use.

As shown in FIGS. 1 and 2, the present invention comprises an elongated member 1 with a harness means 2 on one end and a handle 3 on the other end. A slider assembly 4 is located in between the handle 3 and the harness 2. The slider assembly 4 comprises a slider 5, a first connecting member 6, possibly with a hollow portion 7, a second connecting member 8, and a fulcrum 9.

The slider 5 is slideably attached to the elongated member 1. The first connecting member 6 is fixedly attached to the slider 5. The second connecting member 8 can be fixed at a plurality of positions relative to said first connecting member.

In the instance where the first connecting member 6 has a hollow portion 7, the second connecting member 8 is of a diameter such that it can be slideably located at a plurality of positions within the hollow portion 7. The fulcrum 9 is fixedly attached to the second connecting member 8 and rests on the top of the patient's leg. The fulcrum 9 may comprise a cushion or pad 10 attached to a base 11, which should be constructed of some rigid material.

The slider assembly 4 is fully adjustable to allow the fulcrum 9 to be placed either above or below the knee joint and also to accommodate persons of varying heights and leg lengths. Additionally, the second connecting member 8 can slide in and out of the hollow member 7, thereby allowing adjustment of the distance between the fulcrum 9 and the slider 5. Placing the fulcrum 9 further from the slider 5, i.e. higher on the leg relative to the attachment point of the slider assembly 4, allows for increased leverage on the order of 300–500% which allows a patient to exert higher pressures to straighten the leg without the use of weights or assistance of another.

The slider assembly 4 may include a locking means 12 for securing the position of the fulcrum relative 9 to the slider 5. The harness means 2 comfortably supports the foot, in particular the heel and ankle. Finally, the fulcrum 9 is fixedly attached to the second connecting member 8 such that a full range of motion can be obtained.

The present invention offers more flexibility than the prior art. No prior art has the range of adjustment that the present invention offers, nor does any of the prior art allow for increased leverage without the use of weights. The present invention provides for greater support of the heel and ankle than any prior art. The present invention also avoids direct contact with the knee joint and also incisions from surgery. This is particularly important, as direct pressure on the knee joint could be harmful to the joint. Additionally, since most knee surgeries involve incisions which are normally closed with staples and/or stitches, direct pressure on the incision would not only put the user in excruciating pain, but would likely rupture the incision. It is obviously preferable to utilize a fulcrum located either above or below the knee, thereby eliminating direct pressure on the knee joint and/or incision(s), while still allowing the knee joint to be effectively exercised.

BEST MODE CONTEMPLATED BY THE INVENTORS

As shown in FIGS. 3 and 4, the Best Mode contemplated by the inventors utilizes square tubing for the elongated member 1. The handle 3 is J-shaped, and both ends of the elongated member 1 are fitted with plugs 14. The harness means 2 comprises two straps 15 and uses a ring 13 to tighten the harness on the users foot and ankle. The slider 5 is made of square tubing to facilitate movement along the elongated member 1. The first connecting member 6, which is welded to the slider 5, is made of round tubing and is L-shaped, with the hollow portion 7 attached to the shorter end. The hollow portion 7 is also made of round tubing and is of a diameter slightly larger than that of the first connecting member 6. The second connecting member 8 is also L-shaped and is made of round tubing of diameter slightly smaller than the inside diameter of the hollow portion 7, thereby allowing the second connecting member 8 to slide in and out of the hollow portion 7. A hand knob 12 is located on the top of the hollow portion 7 to fix the position of the second connecting member 8. The fulcrum 9 is attached to the short end of the second connecting member 8 and comprises a base 11 made a rigid material, such as aluminum, and a cushion or pad 10 attached to the bottom portion or said base 11. The fulcrum 9 is curved, so as to fit the user's leg.

We claim:

1. A device for exercising a leg and/or knee joint comprising:

an elongated member having a first end and a second end;

said first end forming a handle and said second end having a harness means attached thereto;

a slider assembly slideably attached between said ends of said elongated member;

said slider assembly comprising:

a slider, which slides along said elongated member;

a first connecting member fixedly attached to said slider;

a second connecting member; and a fulcrum fixedly attached to said second connecting member.

2. The device of claim 1;

said slider assembly having a means for fixing the position of the second connecting member relative to the first connecting member.

3. The device of claim 2;

said slider assembly having a means for fixing the position of the slider relative to the elongated member.

4. The device of claims 2;

said first connecting member being L-shaped, having a first end, a first straight portion, a second straight portion, and a second end;

said first straight portion being disposed between said first end and said second straight portion;

said second straight portion being positioned at an angle relative to said first straight portion; and said second straight portion being disposed between said first straight portion and said second end;

said second connecting member being L-shaped, having a first end, a first straight portion, a second straight portion, and a second end;

said first straight portion being disposed between said first end and said second straight portion;

said second straight portion being positioned at an angle relative to said first straight portion; and said second straight portion being disposed between said first straight portion and said second end.

5. The device of claim 1;

said first connecting member having a hollow portion;

said hollow portion oriented at an angle relative to said first connecting member;

a second connecting member, having a diameter such that it can be slideably located at a plurality of positions within said hollow portion; and a means for fixing the position of said second connecting member relative to said first connecting member.

6. The device of claim 1;

said fulcrum having a cushion means attached to the bottom of said fulcrum so as to rest on the user's leg.

7. The device of claims 1;

said first connecting member being L-shaped, having a first end, a first straight portion, a second straight portion, and a second end;

said first straight portion being disposed between said first end and said second straight portion;

said second straight portion being positioned at an angle relative to said first straight portion; and said second straight portion being disposed between said first straight portion and said second end;

said second connecting member being L-shaped, having a first end, a first straight portion, a second straight portion, and a second end;

said first straight portion being disposed between said first end and said second straight portion;

said second straight portion being positioned at an angle relative to said first straight portion; and said second straight portion being disposed between said first straight portion and said second end.

* * * * *